US006690159B2

(12) United States Patent
Burreson et al.

(10) Patent No.: US 6,690,159 B2
(45) Date of Patent: Feb. 10, 2004

(54) POSITION INDICATING SYSTEM

(75) Inventors: Bernard Burreson, Seattle, WA (US); Patrick A. Knappert, Lynnwood, WA (US); Kevin G. Woolsey, Snohomish, WA (US); Jeff Lamping, Mountlake Terrace, WA (US); Alan Orr, Woodinville, WA (US)

(73) Assignee: Eldec Corporation, Lynnwood, WA (US)

( * ) Notice: Subject to any disclaimer, the term of this patent is extended or adjusted under 35 U.S.C. 154(b) by 149 days.

(21) Appl. No.: 09/810,083

(22) Filed: Mar. 16, 2001

(65) Prior Publication Data

US 2002/0077752 A1 Jun. 20, 2002

Related U.S. Application Data

(63) Continuation-in-part of application No. 09/706,434, filed on Nov. 3, 2000.
(60) Provisional application No. 60/235,988, filed on Sep. 28, 2000.

(51) Int. Cl.[7] .............................. G01B 7/14; G01B 7/30; G01D 5/12
(52) U.S. Cl. ............................ 324/207.23; 324/207.24; 324/207.25; 324/207.12
(58) Field of Search ........................ 324/207.23, 207.24, 324/207.25, 207.12, 207.2, 207.21; 338/32 H, 32 R; 73/314; 74/471 XY; 702/95

(56) References Cited

U.S. PATENT DOCUMENTS

| 4,197,855 A | * | 4/1980 | Lewin ...................... 338/32 H |
| 5,003,260 A | | 3/1991 | Auchterlonie |
| 5,285,154 A | | 2/1994 | Burreson |
| 5,351,004 A | | 9/1994 | Daniels et al. |
| 5,589,769 A | | 12/1996 | Krahn |
| 5,734,130 A | | 3/1998 | Baker |
| 6,100,681 A | | 8/2000 | Tsuruta |

FOREIGN PATENT DOCUMENTS

| EP | 0 439 912 A2 | 8/1991 |
| EP | 0 590 222 A1 | 4/1994 |
| EP | 0 595 553 A1 | 5/1994 |
| GB | 2 226 720 A | 7/1990 |
| WO | WO 92/08176 A1 | 5/1992 |

\* cited by examiner

Primary Examiner—Walter E. Snow
(74) Attorney, Agent, or Firm—Christensen O'Connor Johnson Kindness PLLC

(57) ABSTRACT

A target device is carried by or mounted on a first part movable relative to a second part. The second part has a sensing device including an array of sensors providing outputs responsive to the magnet field of the target device. A processing device receives the outputs of the sensors and calculates relative positions of the two parts based on the outputs.

29 Claims, 15 Drawing Sheets

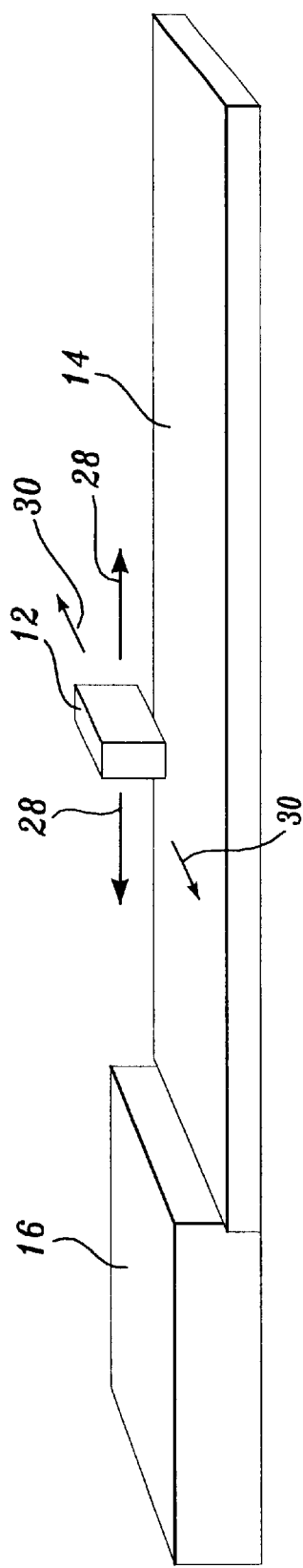
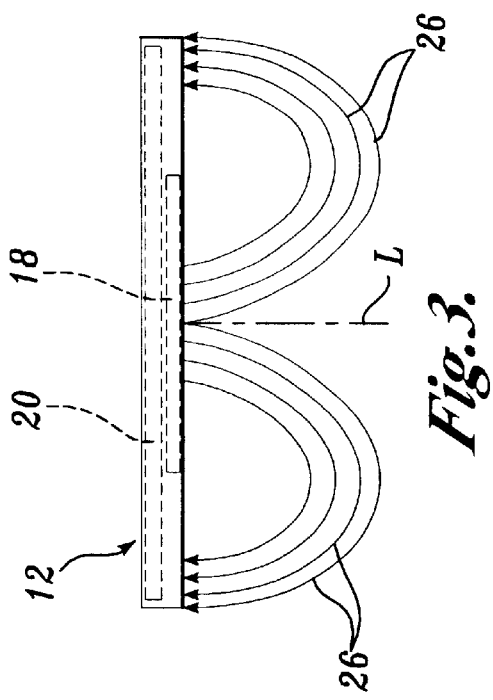
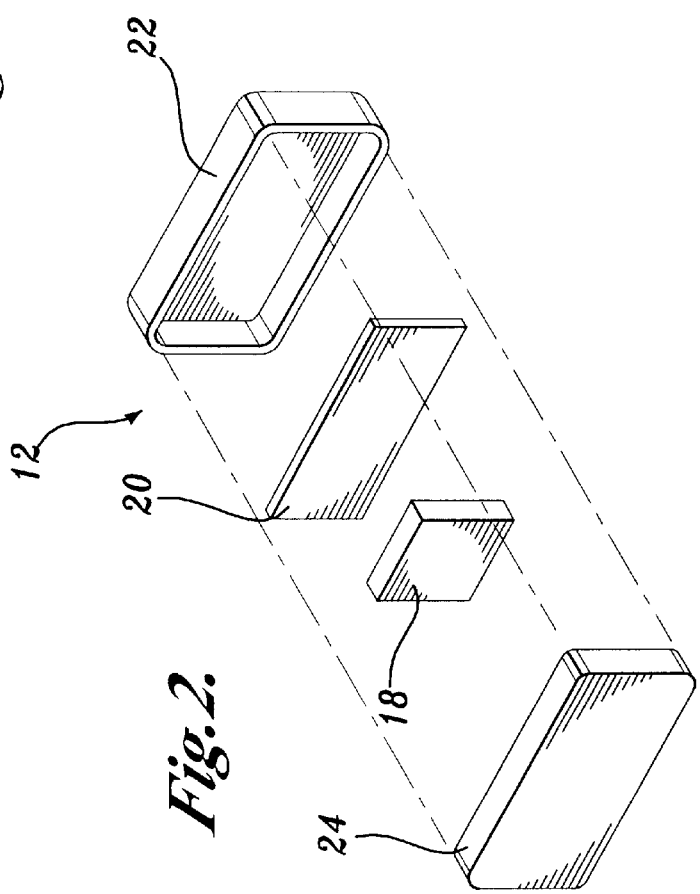
Fig.1.
Fig.2.
Fig.3.

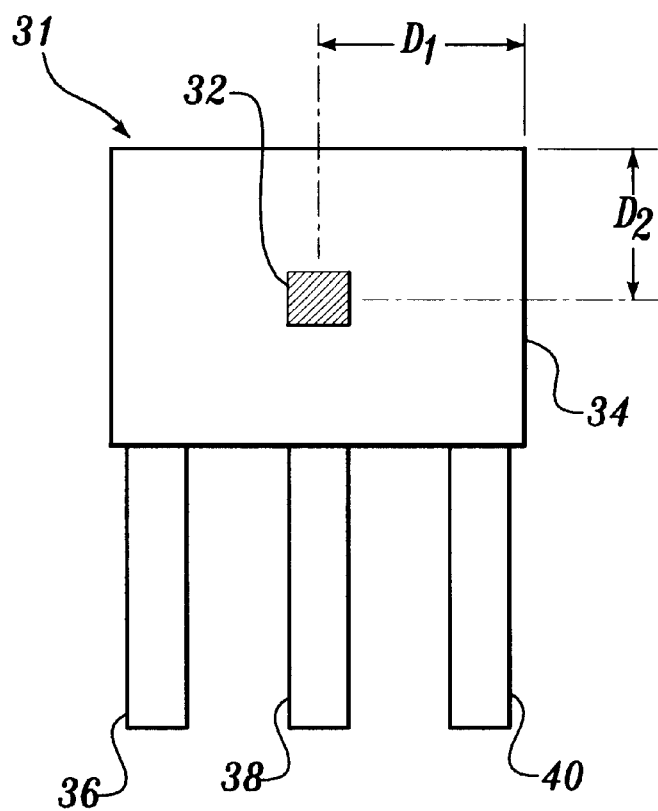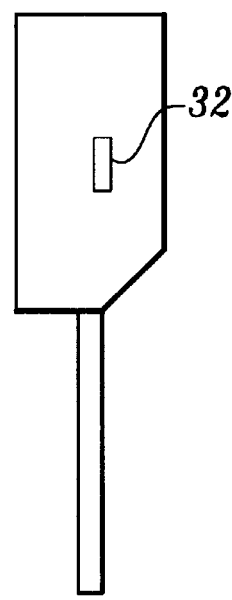
*Fig.4.*   *Fig.5.*

POSITION INDICATING SYSTEM

CROSS-REFERENCE TO RELATED APPLICATIONS

This application is a continuation-in-part of copending application Ser. No. 09/706,434, filed Nov. 3, 2000, which claims the benefit of U.S. Provisional Application No. 60/235,988, filed Sep. 28, 2000.

FIELD OF THE INVENTION

The present invention pertains to a system for detecting the position of one part relative to another without any contact between the two parts. For example, one of the parts can be a "target device" movable relative to a "sensing device," and the two parts can be incorporated in or mounted on adjacent, relatively movable components of a mechanical system.

BACKGROUND OF THE INVENTION

In the aircraft industry, which is one industry with which the present invention is concerned, there are a variety of situations in which it is desired or essential to know the position of one mechanical component relative to another. "Position" can include the location of one part relative to another (X, Y, and Z coordinates in a Cartesian coordinate system, for example), and/or the attitude of one part relative to another (degree of relative pitch, yaw, and/or roll). For example, for optimum performance it may be necessary to know the degree of extension or retraction of an actuator, which may correspond to the position of a flight control surface such as a leading edge or trailing edge flap, aileron, rudder, or horizontal stabilizer, or the orientation of a nose wheel, or any of a variety of other components. Depending on the actuator or component, different position sensing or indicating systems have been used. For example, if the actuator is of the screw type and run by a motor, electromechanical counters may be used to estimate position by the number of turns that the screw type actuator has been driven. In another case, inductive sensors have been used, primarily linear variable differential transformers (LVDTs), where the change in coupling between primary and secondary coils is measured to indicate the position of a magnetically permeable rod run through a core. The ends of the LVDT can be connected to devices whose relative location it is desired to measure. Other known location sensing examples include electronic calipers and optical encoders.

In general, known sensing systems require very close and controlled spacing between the components whose relative positions are being measured. These are also subject to inherent accuracy tolerances which, ideally, should be reduced, and/or have other disadvantages such as temperature or pressure variations, or sensitivity to environmental conditions such as dust, wind, grit, electronic noise, and so on. Using an LVDT as an example, an LVDT system can be sensitive to temperature variations, must move in a linear fashion, require precise alignment, is sensitive to cable length, usually requires protection from dirt or ice, and can be sensitive to noisy electronic environments.

In contrast to true position sensing systems, there are known proximity sensors that will indicate the close presence of one object relative to another. LVDTs have been used for proximity sensing applications, as well as Hall effect sensors of the type that provide an output as a function of magnetic field strength. In the absence of structure interfering with the presence or detection of a magnetic field, a Hall effect sensor may be used to detect the fact that a component having a magnetic target has been moved close to a component on which a Hall effect sensor has been mounted. Examples of proximity sensing systems are described in U.S. Pat. Nos. 5,285,154 and 5,351,004. These patents also describe embodiments for sensing distance within a limited range.

SUMMARY OF THE INVENTION

The present invention provides a highly accurate position (location and/or attitude) sensing system which can be used for noncontacting objects or parts that are moved relative to each other, and which is operable in environments hazardous to other sensing systems, is very insensitive to temperature variations or noisy environments, can move in nonlinear, curved, or twisting directions, and needs no protection against dirt or ice.

In one aspect of the present invention, a target device is carried by or mounted on one of the parts. This target includes one or more magnets creating a magnetic field. The present invention also includes a sensing device carried by or mounted on the other of the parts, which contains an array of Hall effect sensors for detecting the magnetic field. For example, in a one dimensional or "linear" sensing system, the Hall effect sensors can be arranged in one or more rows extending lengthwise in the sensing direction, such direction being the direction along which the target device is moved relative to the sensing device. In such a system, the individual outputs of the Hall effect sensors are electronically scanned and processed to determine the location of the target relative to the sensing device. This can involve grouping the sensors and providing their outputs to a series of multiplexers which, in turn, are connected to a processor for analyzing the outputs and computing the location of the target.

More specifically, the processing of the individual Hall effect sensor outputs can include determining which Hall effect sensor has the highest output, corresponding to the location of the greatest magnetic field strength, and limiting the processing to the output of that Hall effect sensor and a predetermined number of sensor(s) at each side. The analog outputs of the selected sensors are converted to digital information that is evaluated mathematically to determine the target location. Depending on the requirements of a particular application, different error correction algorithms may be used for a desired degree of accuracy or failure mode correction.

Other methods are also used to determine the correct set of Hall effect sensors to evaluate for position. One such method is correlation. In this method, a vector of values corresponding to the desired signal is mathematically correlated against the vector signal set from scanned Hall effect sensors. A peak in the correlation signal indicates the center of the desired set to evaluate. This method works well when dealing with possible failed Hall elements.

Additionally, the detection system need not be the peak signal and adjacent Hall devices, but instead or in addition, one might desire to look at the zero crossing signal which results from using combinations of north and south magnets.

In another aspect of the invention, the system can be adapted for measuring or tolerating variations in the location of the target perpendicular to the normal sensing direction. In such a system the normal sensing direction can be referred to as the X direction, a direction transverse to the sensing direction but parallel to the sensing device can be referred to as the Y direction, and the direction perpendicular to the sensing device can be referred to as the Z direction. The system of the present invention is adaptable to large tolerances in the Y and Z directions while still providing accurate X direction measurements, such that precise alignment of the parts is not always required. The X direction travel need not be straight and flat, but can follow arcs, curves or twisting surfaces.

In still another aspect of the present invention, the system is adapted for measuring the location of the target in two dimensions (such as X and Y) and/or three dimensions (X, Y and Z), or any other coordinate system. In addition, a system in accordance with the present invention can be used to measure relative attitude (pitch, yaw, and/or roll positions).

Error correction can be used to compensate for manufacturing tolerances, such as unavoidable impreciseness in the positioning of the Hall effect sensors' physical locations and unavoidable tolerances in the outputs of the Hall effect sensors themselves, which include variable gains and voltage offsets.

In another aspect of the invention, the system can be adapted for detecting the rotational angle, the speed of rotation, or the acceleration, of a swinging or rotatable component.

Because of the ability of this system to look through nonmagnetic materials, one of this system's major attributes is that both the sensor and the target can be sealed, and thus function in hazardous environments and/or harsh environments. Detection areas such as chemical or fuel cells, or high pressure or high temperature environments can be accommodated.

In most instances, positional error of systems like LVDT's is expressed in percent error of stroke length. This results in larger absolute errors for longer stroke sensors. The present invention has a very small error initially, and that error is constant regardless of stroke length. As a result, for longer stroke devices of the present invention, the percent error of stroke decreases as the sensing length increases.

The present invention uses a computational device like a micro-controller. This device and its associated electronics (power supply, I/O, analog-to-digital converter) can be either integrated with the sensor, or moved remote. Sometimes it is advantageous to move some of the electronics to a more benign environment to increase overall reliability and reduce system costs.

Another significant advantage of this invention is that the sensor can track several targets at the same time. This feature allows the invention to perform unique features such as measure special targets of lengths far greater than the sensor, average many targets for reduced error, or correct off axis rotation speed wobble on a circular sensor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 is a diagrammatic top perspective of noncontacting position indicating components in accordance with the present invention, including a target device, a sensing or "data acquisition" device, and a processing or "computation" device;

FIG. 2 is a diagrammatic representation of a typical target device usable in the present invention, with parts in exploded relationship; and FIG. 3 is a diagrammatic side elevation of the target device with parts assembled;

FIG. 4 is a diagrammatic top plan of an individual Hall effect sensor usable in a sensing device in accordance with the present invention; and FIG. 5 is a diagrammatic side elevation of the sensor of FIG. 4;

DETAILED DESCRIPTION OF THE PREFERRED EMBODIMENT

Figure 6:
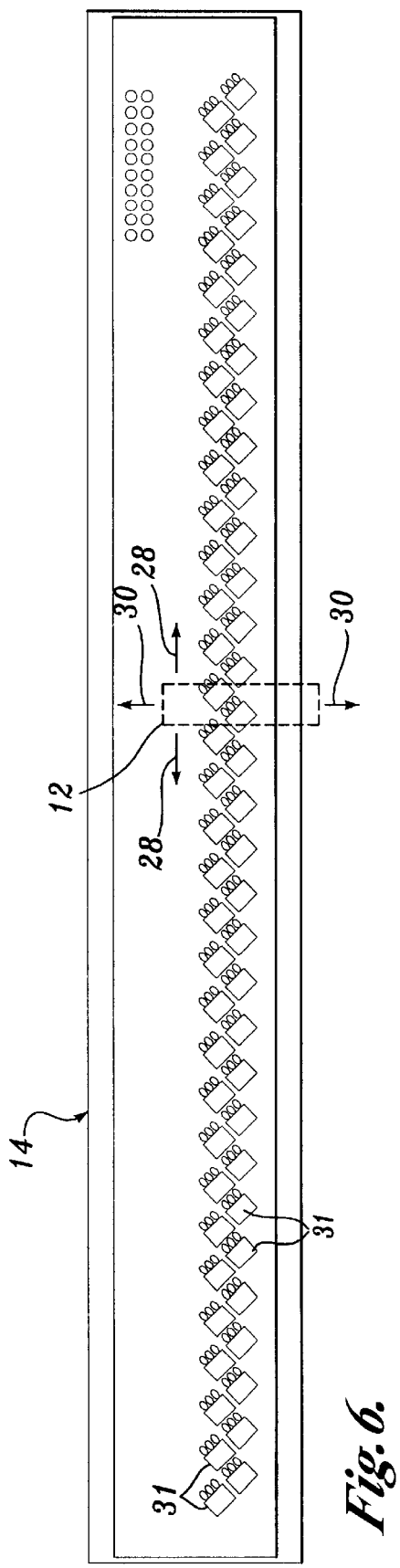
FIG. 6 is a top plan of a sensing device usable in a system in accordance with the present invention, using an array of Hall effect sensors.

A first embodiment of the present invention is used to detect the location of a first part relative to a second part, such as relatively movable components of a mechanical system. With reference to FIG. 1, one of such parts can carry or have embedded in it a target device 12 and the other of such parts can have mounted on or embedded in it a sensing device 14 also referred to as a data acquisition device. The sensing device provides signals to a processing or computation device 16 which, based on the output of the sensing device, computes the location of the target device relative to the sensing device.

In this embodiment, the target device incorporates a magnet and the sensing device includes an array of sensors, preferably Hall effect sensors, providing outputs that vary as a function of the strength of the magnetic field induced by the target device. The outputs of several sensors are provided to the processing device that evaluates the outputs to compute the location of the target device.

A representative target device 12 is shown diagrammatically in FIGS. 2 and 3. The primary component is a permanent magnet 18 which can be mounted on an elongated base plate 20 of magnetically permeable material. The base plate, in turn, can be mounted in a container 22 of nonmagnetic material, and the container closed by a cover 24 of nonmagnetic material. The composite target assembly 12 is shown diagrammatically in side elevation in FIG. 3. By incorporating the base plate of magnetically permeable material, the magnetic flux lines 26 are concentrated in a direction away from the base plate 20. Except at very close range, the greatest magnetic flux density is present at the center of the magnet and extends perpendicular thereto as represented by line L in FIG. 3. In general, the flux density decreases as a near Gaussian distribution function as one proceeds away from the magnet center line in the X-Y plane of the magnet. The field decreases in a near hyperbolic function as one proceeds away in a Z direction perpendicular to the magnet face. More details concerning suitable magnet assemblies are described in U.S. Pat. No. 5,285,154 and U.S. Pat. No. 5,351,004. Both of these patents deal with magnetic targets used in proximity sensors, as compared to the present invention in which a magnetic target is used in a location indicator. While the general construction shown in FIGS. 2 and 3 can be used in the present invention, it should not be considered to be limiting. The important aspect is that the target device incorporates a magnet, with a magnetic field having a flux density which has a maximum at or adjacent to the center of the magnet and which decreases as a function of the distance moved away from the magnet. A single thin magnet can be used, or an array of magnets located side by side. The magnet or array of magnets then can be mounted in the container, such as an aluminum housing, and sealed. Hermetic sealing in a highly conductive material such as aluminum is preferred. The assembled target device can be mounted on or incorporated in a part whose location relative to another part is to be measured or monitored.

In the embodiment of FIG. 1, it is preferred that the magnet or magnet array of the target device 12 be elongated transversely of the sensing direction. The sensing direction is represented by the arrows 28 and can be referred to as the X direction. The transverse direction of elongation of the target device 12, indicated by the arrows 30, can be referred to as the Y direction. In this case, the magnetic field will be fairly uniform in the Y direction for a distance approximately equal to the length of the target device, i.e., assuming that the magnet or magnet array extends the full length of the target device in the Y direction. Thus, if the target device is shifted slightly in the Y direction, there will be little or no variation in magnetic field strength along a line that extends in the X direction and intersects the face of the target device adjacent to the sensing device. As discussed in more detail below, this allows for substantial variation in the position of the target device in the Y direction without substantially affecting the accuracy for measurement of the location of the target device in the X direction. This embodiment is already very immune to variances in magnetic field strength, thus this target design feature simply enhances the product further for large target movements. The longer the magnet or array of magnets of the target device, the more variance in the Y direction can be tolerated.

The currently preferred magnet material is Samarium Cobalt because it is a high-energy material with good temperature characteristics, important for aerospace applications. For lower temperature environments, other materials such as neodymium or Iron Boron can be used. As discussed in more detail below, the design and more particularly the strength of the magnet will depend on the sensing device with which it is matched. Since the present sensing device uses Hall effect sensors, accuracy would be affected, in the peak detecting method described below, if the flux density of the magnetic field was great enough to saturate the sensors of the Hall effect devices. The alternative zero crossing detection method described below takes advantage of the saturation. A combination of both detection methods could be used.

For a one-dimensional or linear sensing device of the type illustrated diagrammatically in FIG. 1, a linear array of Hall effect devices is used in the sensing device 14. Thus, known Hall effect transducers can be placed side by side in a single row in the sensing or X direction. For greatest accuracy, it is desirable for the sensors of the Hall effect transducers to be located close to each other in the X direction. However, the distance between adjacent Hall effect devices is affected by the casings and housings in which they are mounted. For example, current prototypes of the present invention use a model A3515LUA ratiometric, linear Hall effect sensor available from Allegro Microsystems, Inc. of Worcester, Mass. FIG. 4 illustrates the physical layout of such a Hall effect device 31, the small sensing component 32 being approximately centered in a rectangular housing 34. Pins or contacts 36, 38 and 40 project from the housing for connection to the supply voltage, ground and output, respectively. The distance D1 from the center of the small sensing component 32 to the end of the housing in its long dimension is 0.081 inch (2.06 mm) and the distance D2 from the center of a sensing component 32 to the edge of the housing in the short dimension direction is 0.056 inch (1.42 mm). Thus, if the housings are placed end to end with their pins projecting in the same or alternate directions, the center to center distance between adjacent centers will be at least 0.162 inch (2.12 mm). This distance can be reduced by providing a sensing device 14 with an array of the type shown in FIGS. 6 and 7, which are diagrammatic top plans of a printed circuit board B in which an array of the Hall effect sensors 31 is mounted. The housings of sensors 31 are canted at an angle of 45° to the sensing or X direction, and are provided in two rows with the sensors staggered relative to each other. This reduces the center to center distance D3 between adjacent sensing components 32 by a factor of 0.707, for increased accuracy in locating a target device 12 moved relative to the sensing device 14 in the X direction. In this embodiment, it is preferred that the target device be sufficiently wide in the Y direction that the magnetic field is uniform for a Y dimension distance exceeding the distance between the center points of sensors of the different rows, with a greater width being used for a greater tolerance of possible shifting or misalignment of the target device in the Y direction. Higher linear component density can be accommodated by angles lower than 45° thus allowing more units in the Y direction.

The Hall effect devices 31 are sensitive, temperature-stable linear Hall effect sensors operating at a typical supply voltage (at pins 36) of 5 volts. The devices are designed to provide an output voltage of 2.5 volts in the absence of a detectable magnetic field. The presence of a south pole magnetic field will increase the output voltage at pin 40 above 2.5 volts by an amount proportional to the magnetic field applied within a predetermined range of magnetic field strength. Conversely, the application of a north pole magnetic field will decrease the output voltage from its quiescent value of 2.5 volts proportional to the magnetic field applied.

Figure 7:
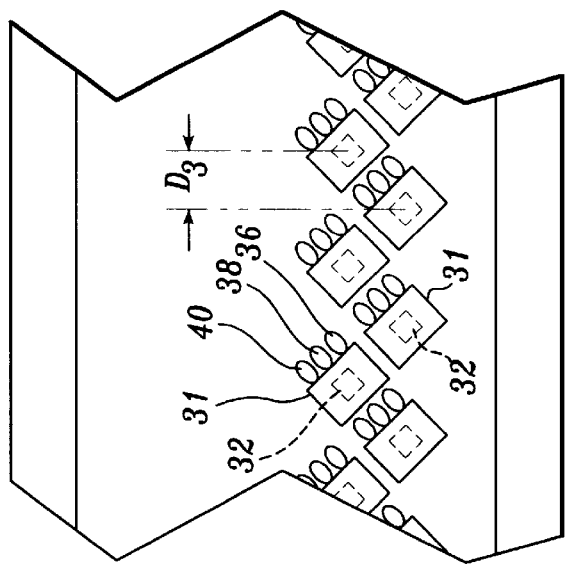
FIG. 7 is an enlarged, fragmentary top plan of the FIG. 6 sensing device.
Figure 8:
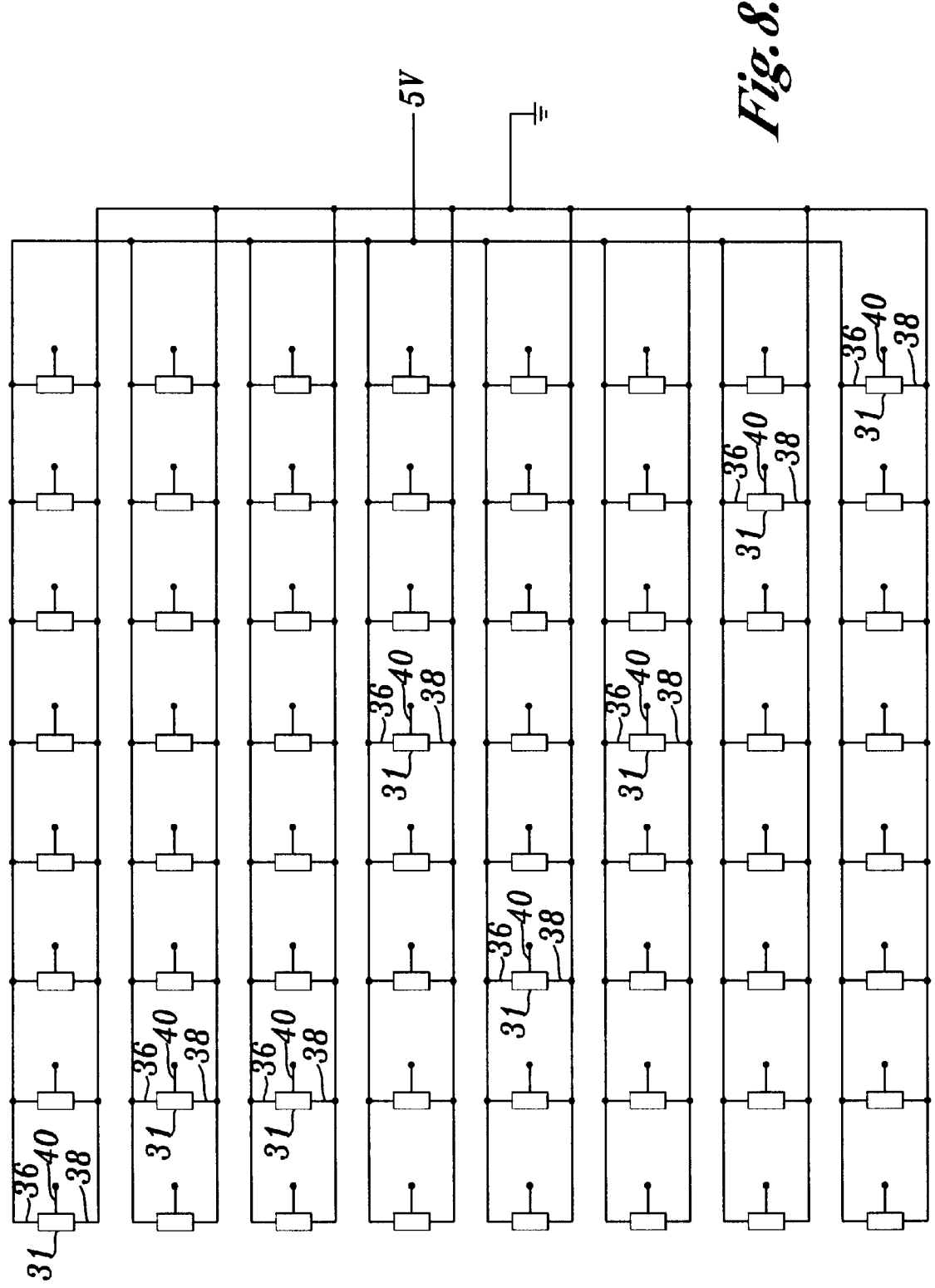
FIG. 8 is a block diagram of part of the circuit for the sensing device of FIGS. 6 and 7.
Figure 9:
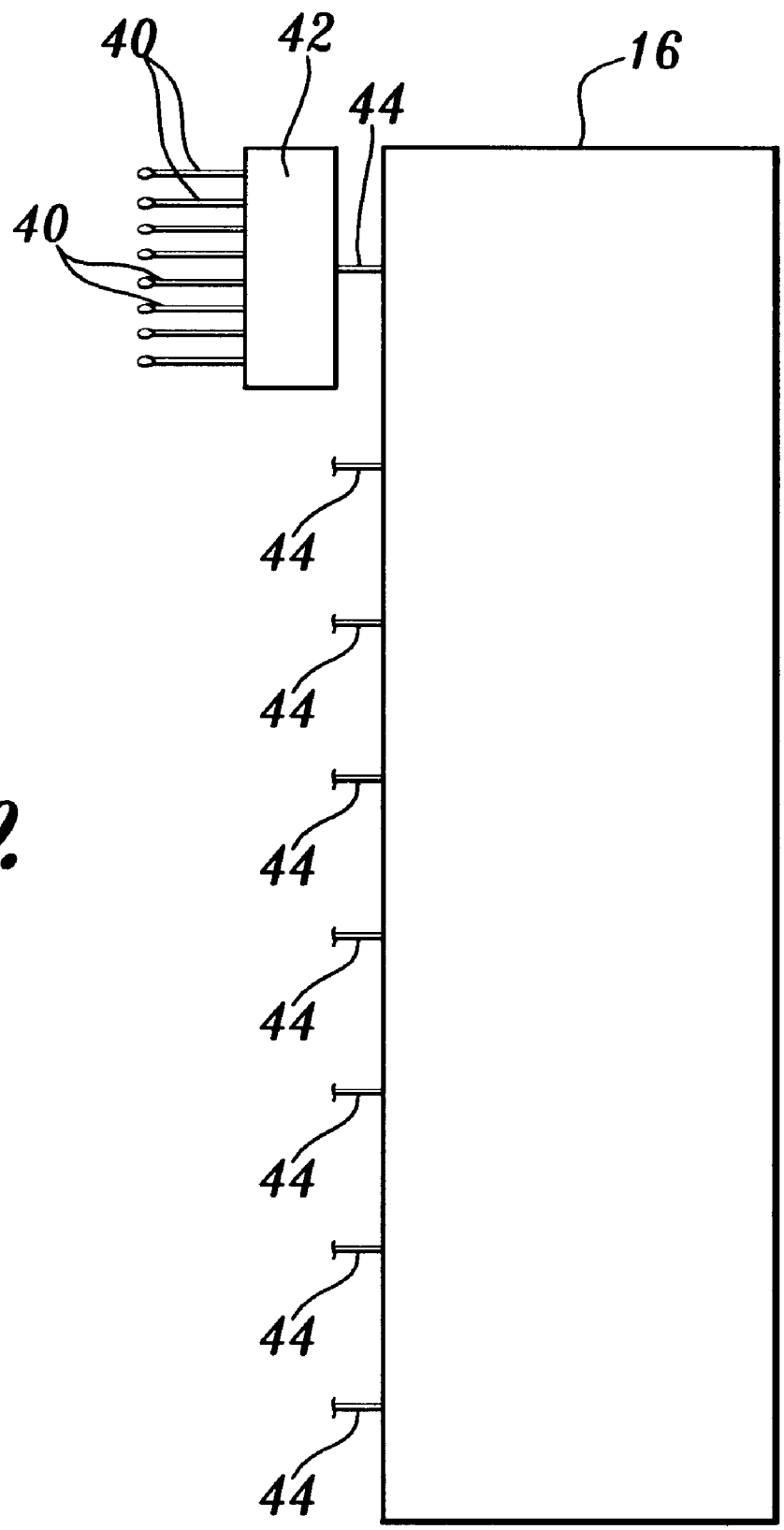
FIG. 9 is a block diagram of another aspect of the circuit illustrating its interconnection with a processing or computation device.

In the embodiment illustrated in FIGS. 6 and 7, 64 sensing devices 31 are provided along the sensing direction, 32 in each row. All of such devices are mounted on a single printed circuit board. The digital ground and supplies lines are isolated from the analog ground and supply lines for noise reduction purposes. The analog portion is shown and, with a common voltage supply and ground, as represented by the circuit diagram of FIG. 8. The printed circuit board also can include multiplexers for scanning of the outputs of the sensing devices. For example, in the case of 64 sensing devices, eight eight-port multiplexers can be used, one such multiplexer 42 being represented in FIG. 9, coupled to a computation device 16, namely, a microprocessor. A ninth multiplexer is used to take the output of the eight multiplexers to one output for the analog-to-digital converter. Each multiplexer 42 receives the outputs on pins 40 from eight of the Hall effect sensors and provides a selected output on a line 44 to the microprocessor. The microprocessor includes an analog-to-digital converter that, in combination with the multiplexers, scans the outputs of the 64 sensing devices and converts them to digital form. The microprocessor also stores the algorithm by which the Hall array outputs are processed to determine the location of the target device relative to the sensing device.

In one embodiment of the present invention, processing of the outputs of the individual Hall effect sensors is accomplished by scanning all device outputs and determining which of them has the "highest" value. For this purpose, "highest" means the maximum difference from the quiescent value, i.e., the degree to which the output voltage has been shifted up or down from the quiescent voltage of 2.5 volts. "Highest" can also refer to the point in the Hall array where a predetermined signal vector produces the highest correlation against the scanned Halls. The outputs of a predetermined number of sensors at each side of the "highest" signal are also considered, such as three sensors at each side or four sensors at each side. The outputs of the remaining sensors are ignored. This predetermined number of outputs is used to calculate the target location. The specific algorithm or algorithms used will depend on the accuracy desired.

Figure 10:
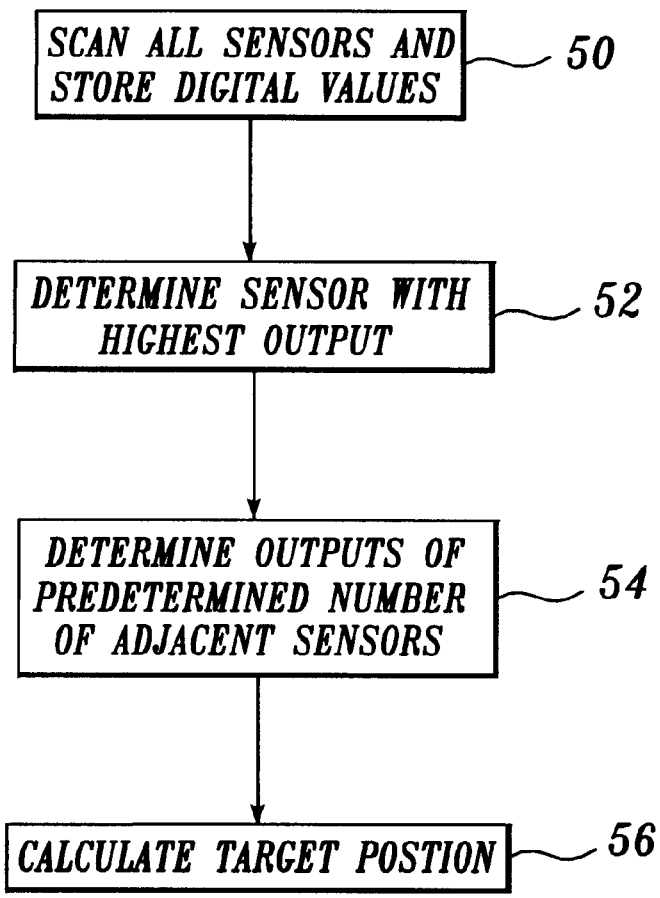
FIG. 10 is a flow diagram of aspects of a method for calculating the relative positions of two parts in accordance with the present invention.

The general method is illustrated in FIG. 10. The outputs of all sensors are scanned and stored by the microprocessor as indicated by box 50. Next, the sensor with the "highest" output is determined (box 52) and the outputs of a predetermined number of adjacent sensors are determined (box 54). Then the position of the target device is determined based on the selected outputs (box 56).

Figure 11:
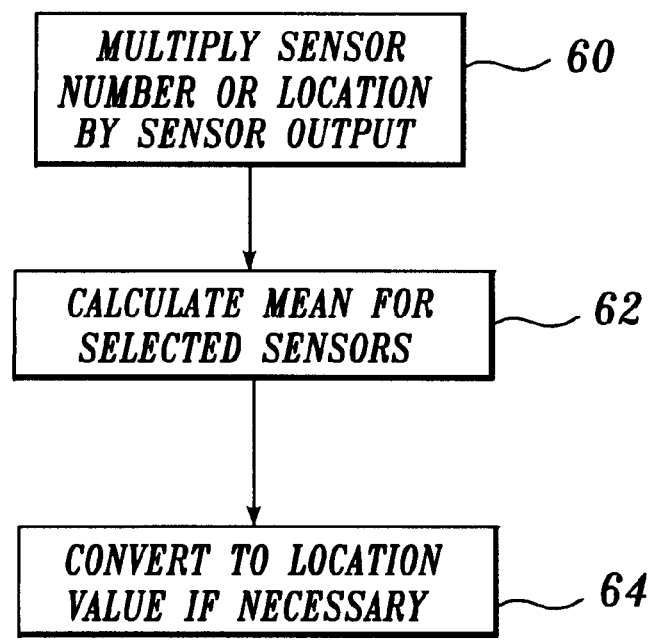
FIG. 11 is a flow diagram of aspects of a modified method for calculating relative positions of two parts in accordance with the present invention.

Stored within the processing device is information concerning the position of each individual sensor. This can be by sensor number, for example, "1," "2," . . . , "64" for a 64-sensor array, which then can be converted to a location value based on the position of that sensor along the length of the sensing device. One simple algorithm for calculating the position of the target device from the selected outputs is represented in FIG. 11. If the sensing device having the highest output is labeled "S," and if the system is designed to consider the outputs of three sensors at each side, such additional sensors can be labeled S-3, S-2, S-1, S+1, S+2 and S+3. The sensor number can be multiplied by its respective output (box 60), and the mean value determined for the selected sensors (box 62). This value then can be converted to a distance or location value for the target device (box 64), if the calculation has been based on the sensor number rather than location. Similarly, if the conversion of sensor number to location already has been made, the location (typically, the distance from one end of the array to the sensor of interest) is weighted by the output of the corresponding sensor, and the mean value determined and used as the indication of the location of the target device. This series of steps corresponds to box 56 of FIG. 10.

However, the above method assumes linear proportionality in variation of magnetic field strength away from the target device in the sensing direction. In actuality, the variation is nonlinear, and more nearly a Gaussian distribution. Consequently, a more accurate result can be obtained by fitting the selected data to a nonlinear function such as a Gaussian distribution curve. In this computation, one of the parameters is the mean of the Gaussian fit, which corresponds to the target location. Commercially available software can be used to calculate an appropriate Gaussian distribution fit, such as TableCurve 2D, available from SPSS Inc. Thus, box 56 of FIG. 10 would include the step of calculating the Gaussian distribution fit and determining the mean.

An even more accurate result would be obtained if the field were truly Gaussian in strength. This may be taken into consideration in target design—the closer the actual field strength distribution is to a Gaussian distribution in the sensing direction, the greater the accuracy would be using this method.

Other parameters of a Gaussian distribution are the spread of the Gaussian signal and the amplitude. Spread calculations can be used for error correction or fault detection. If a given sensor or sensors influence the fit of a distribution curve beyond reasonable parameters, that sensor or sensors can be assumed to be providing erroneous data and be ignored. Amplitude can be used as a basis for determining location of the target in the Z direction.

Approximate Gaussian distributions can be calculated with as few as three sensors (maximum strength sensor and one at each side), requiring less processing power but yielding less accuracy. Depending on the application, the cost savings of reduced processing power may outweigh the reduction in accuracy. Using greater numbers of sensors to perform the calculation can increase accuracy, and can also allow more flexibility in ignoring sensors whose values vary unreasonably from other sensors in the calculation set, for error correction and fault detection purposes.

Another detection method is to observe the zero crossing signal that results from placing a north facing magnet adjacent to a south facing magnet. For example, with reference to FIG. 3, the magnet array 18 could include one or more magnets with north poles facing outward to the left of the centerline L and one or more magnets with south poles facing outward to the right of the centerline L. If the south and north facing magnets or magnet arrays are of the same size and strength, then the resulting magnetic field at the junction is perfectly horizontal to the faces of the magnets. To a Hall device measuring the vertical field component, this would result in a zero reading, i.e., the quiescent output voltage of the Hall device in the absence of a magnetic field. Thus, by using this form of target, one could detect zero crossings rather than peaks, or measure both peaks and zero crossings. By so doing, saturation of the Hall devices at the peak areas could be allowed, thus possibly extending the usable Z range of the system. Using the zero crossing detection method, the signal from the Hall devices is mathematically fitted to a signal shape, and the signal shape zero crossing is computed. When target magnets are in close proximity to each other and are opposite in polarity, the resulting data signal closely resembles a sine function. Thus, to match a sine function, with its shape and zero crossing, to the data, produces accurate position determination. The detection and calculation method could include the steps of scanning all sensors (box 50 of FIG. 10) and storing the corresponding digital values, determining sensors having values offset in opposite directions from the quiescent value and/or determining a sensor having a value closest to the quiescent value (at box 52 of FIG. 10), in which case sensors at opposite sides would indicate opposite polarities, determining outputs of a predetermined number of adjacent sensors (box 54 of FIG. 10), and calculating the target position based on the outputs (box 56 of FIG. 10) such as by determining a sine function fit to calculate the location of the zero crossing.

Any of the methods described above may be used, or combinations of them, but there still are potential inherent error-producing factors in the system. For example, the individual Hall effect sensors are carefully made to tight tolerances. Nevertheless, for a high accuracy application, the variation from sensor to sensor can have an undesirable effect on accuracy of the system. Two of the most common variations are voltage offset and gain. For example, for the Allegro Model A3515LUA Hall effect sensor described above, quiescent voltage output in the absence of a magnetic field may vary between 2.425 volts and 2.575 volts. One way to increase accuracy in the present invention is to scan the sensors in the absence of a magnetic field, determine the amount of voltage offset, if any, for each sensor, and store the offset values. Then, calculating the target position at box 56 of FIG. 10 can include the step of adjusting the output of each sensor by the amount of its offset, prior to calculating the mean or the nonlinear distribution fit (such as the Gaussian or sine function fit).

Similarly, the sensors can be scanned to determine variable gains by applying a "test" magnetic field and comparing the value of each output to a predetermined value or to the mean, after correction for the offset. The output for each sensor then can be adjusted by a factor corresponding to the detected difference in gain.

Figure 12:
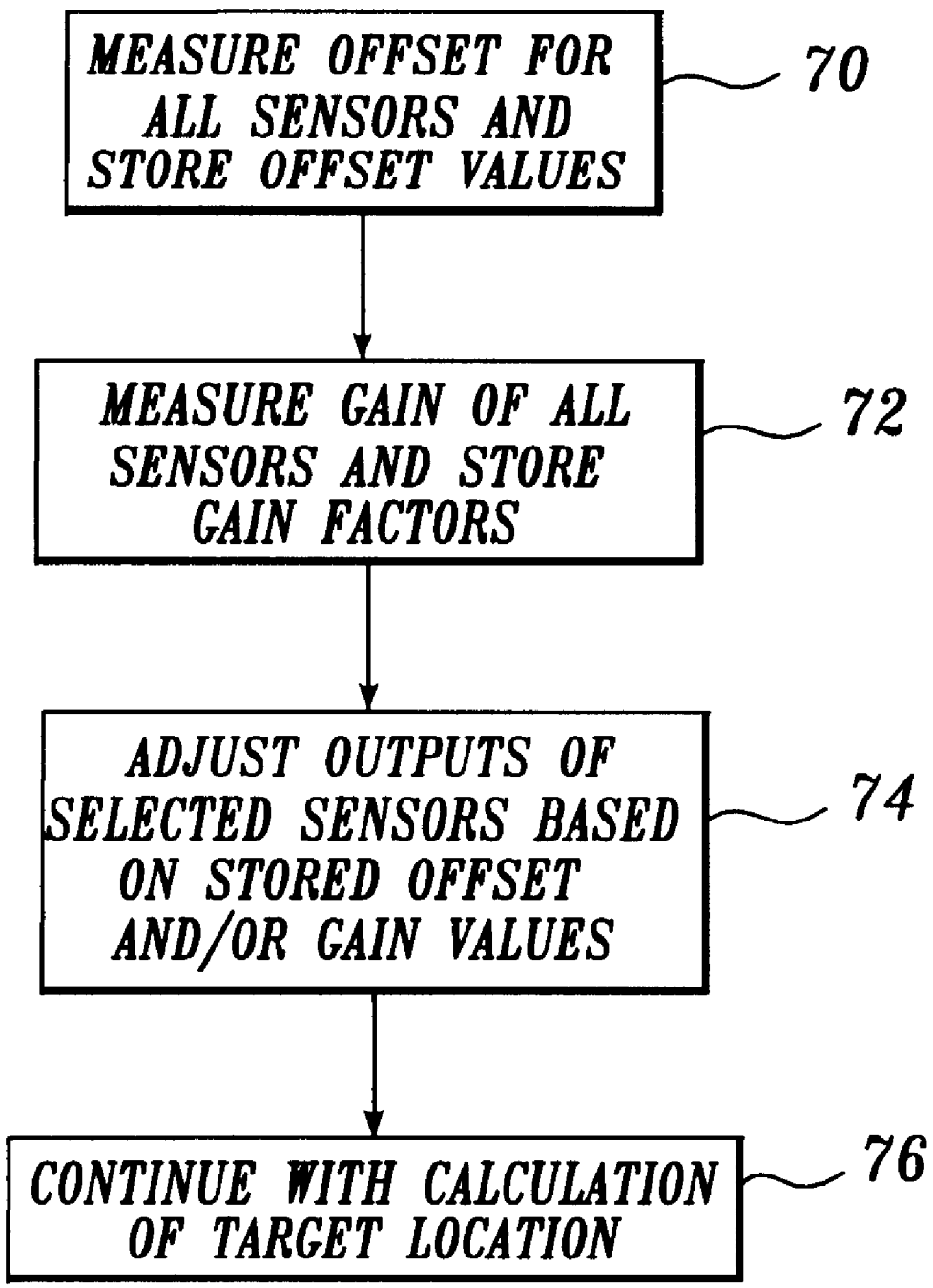
FIG. 12 is a flow diagram of aspects of another modified method for calculating relative positions of two parts in accordance with the present invention.

These steps can be represented as shown in FIG. 12, namely: measure the offsets for all sensors and store the offset values (box 70); measure the gain for all sensors and store the gain factors (box 72); adjust the output values of the selected sensors based on the respective stored offset and/or gain values (box 74); and then continue with the calculation of the target device location (box 76).

Nevertheless, there can remain inherent errors due to the misalignment or mispositioning of the individual sensors. One way to reduce this error is to "calibrate" each sensing device. This can be achieved by performing a series of test scans with a typical or matched target, recording and storing the output response, and calculating an error correction factor or factors which result in minimizing the error. For example, a typical test scan can involve moving the target over the entire sensor array in small steps, such as 0.01 inch, while recording the calculated position at each step using one of the methods described above. The resulting location value can be compared to the known actual value. Once the data has been gathered, an appropriate error reducing algorithm can be performed and a correction value or values stored within the processing unit for that sensing device or combination of sensing device and target device. There are many known algorithms for reducing error once the data set of calculated values to actual values has been determined; one such routine is performed in Matlab using the Optimization Tool set. Small errors can be reduced by fitting the remaining error to error correction polynomial.

The present invention has the ability to measure the location of more than one target at time. Therefore, another way to reduce error is to include two magnets or magnet arrays in the target device, precisely spaced apart a known distance that is greater than the distance between the pre-selected number of sensors used to calculate location for a single magnet or magnet array target device. Stated in another way, the separate magnets or magnet arrays are spaced apart sufficiently that independent location calculations are made without the magnetic field of one magnet part of the target device interfering with the magnetic field of the other magnet part of the target device. In effect, location is determined independently by the separate magnetic fields, and the mean can be calculated which will have the effect of reducing the overall error. While this is an effective method for reducing error and increasing accuracy, it has the disadvantage of requiring very precise location of the magnets or magnet arrays in the target device, and this system also affects the effective sensing range in the X direction because both magnets or magnet assemblies must be offset inward from the ends of the sensor array in order for the independent location calculations to be performed. As discussed below, however, there are other applications for using multiple magnets or magnet arrays spaced apart lengthwise of the target device in the X direction which is very advantageous. If it happens that one is taking advantage of multiple magnet targets, then it makes sense to average as well.

Figure 13:
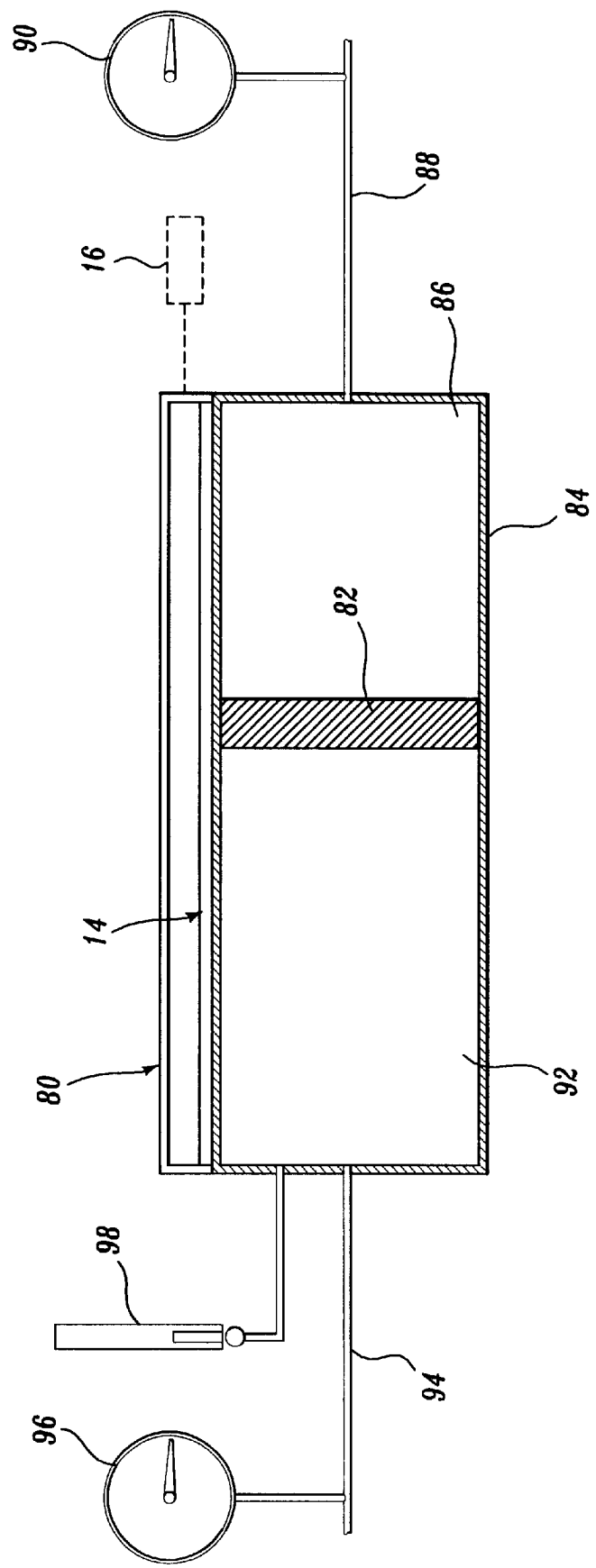
FIG. 13 is a diagrammatic longitudinal section of an accumulator having a position sensing system in accordance with the present invention for detecting the position of the internal accumulator piston.

One significant advantage of the present invention is the ability to "see through" walls of components to locate parts which otherwise are hidden. The Z range distance over which this invention can work is only limited by the ability to measure a signal. Thus the "see through" range can allow for very thick walls. One example is illustrated in FIG. 13, namely a "smart" accumulator 80 in which an internal piston 82 is moved longitudinally inside the accumulator cylinder or housing 84. One end portion 86 of the accumulator is connected to a supply of hydraulic liquid under pressure, such as through a line 88, the pressure being indicated by a gauge 90. The other end portion 92 of the accumulator, i.e., the portion at the opposite side of the piston 82, contains a quantity of gas under pressure communicating with the exterior of the accumulator by a line 94. The pressure is represented by gauge 96 and the temperature of the gas is represented by a temperature sensing device 98. The accumulator precharge for the pressurized gas is defined as the pressure of the gas times the volume divided by the temperature:

$$\frac{PV}{T}.$$

Thus, a truly accurate indication of the precharge requires knowledge of the volume, which depends on the position of the piston. In accordance with the present invention, the piston 82 can be provided with a single magnet target for a non-rotational piston, or a circumferential band of magnets inset in the base of groove for full floating pistons. As discussed above, embedding an annular ring of permeable material in the groove can enhance the magnetic field. The piston housing is formed of a material largely transparent to the magnetic field, such as non-magnetic stainless steel, titanium, or inconel. The sensing array 14 is mounted on the housing and coupled to a processing device 16 for determining the location of the piston 82 with great precision. Consequently, the volume of the gas in accumulator portion 92 is known and, with the pressure and temperature measurements, the precharge of the accumulator is also known.

In the smart accumulator application of FIG. 13, the array of sensors extends substantially the full length of the accumulator housing 84, and is effective to detect the position of the internal piston at any location along the length of the housing. For example, a sensor array of the type described above with reference to FIGS. 6 and 7 may be approximately 9–12 inches long, and usable for an accumulator of approximately that length. For a longer accumulator, either a longer array of sensors would be provided, or the detection range of travel of the piston within the accumulator will be limited to a distance less than the length of the accumulator.

Figure 14:
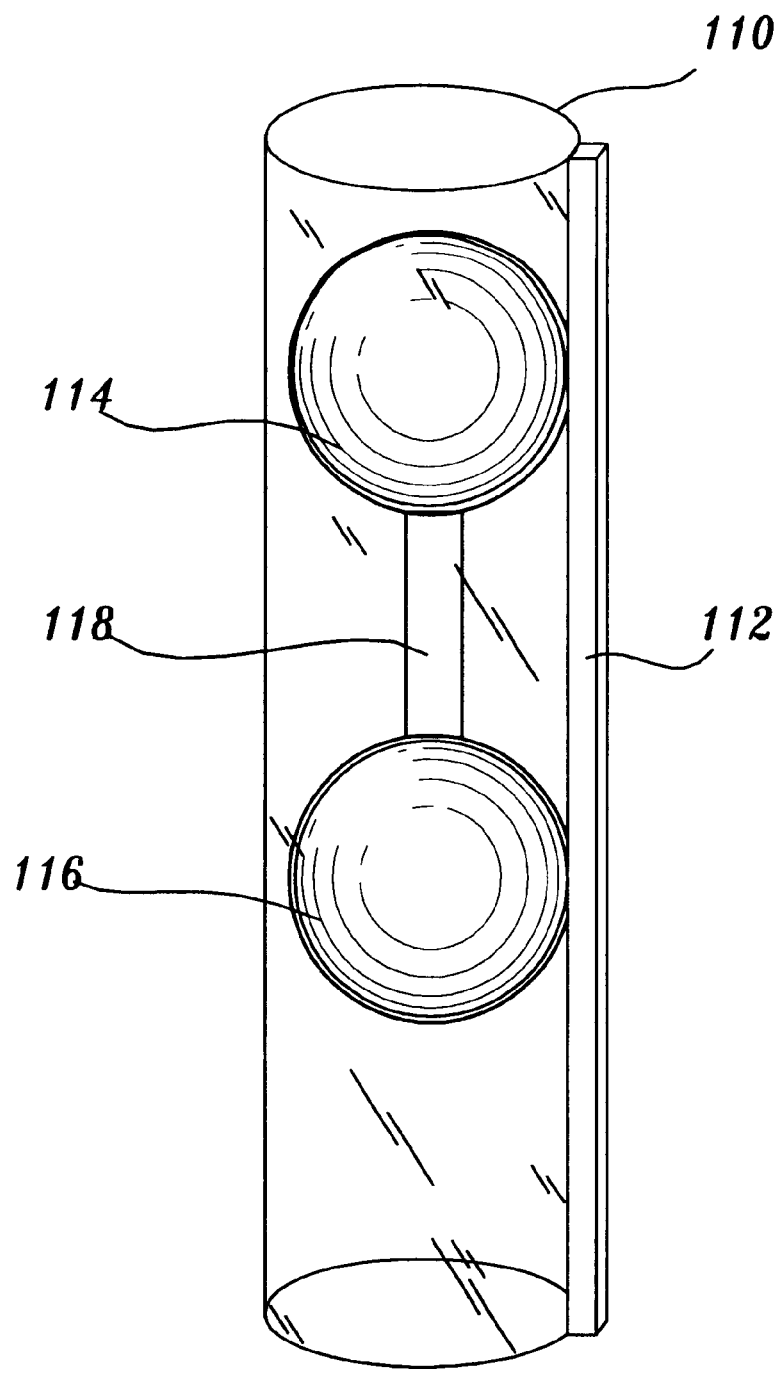
FIG. 14 is a diagrammatic side elevation of a liquid level indicator using the system of the present invention.

The ability of the sensing system in accordance with the present invention to "look through" all nonmagnetic materials, and the ability to sense position precisely without contact between the target device and sensing device, also allows both devices to be hermetically sealed within protective casings and thereby be insensitive to hazardous environments. For example, FIG. 14 illustrates diagramatically a level sensor for liquid within a tube or container 110. The sensing array is sealed within a housing 112, and the target device is sealed within a float 114. A guide member 116 can be connected to the float 114, such as by a connector rod 118. The sensing array sealed within the housing 112 is insensitive to a dirty or otherwise undesirable environment outside the container 110, and the target device sealed within the float 114 is not sensitive to a potentially corrosive or otherwise noxious liquid within the tube or container 110.

Figure 15:
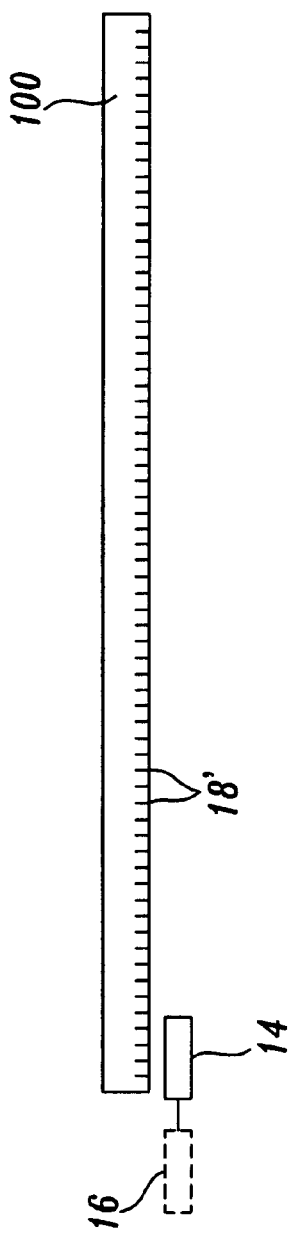
FIG. 15 is a diagrammatic side elevation of another embodiment of noncontacting position indicating components in accordance with the present invention.
Figure 16:
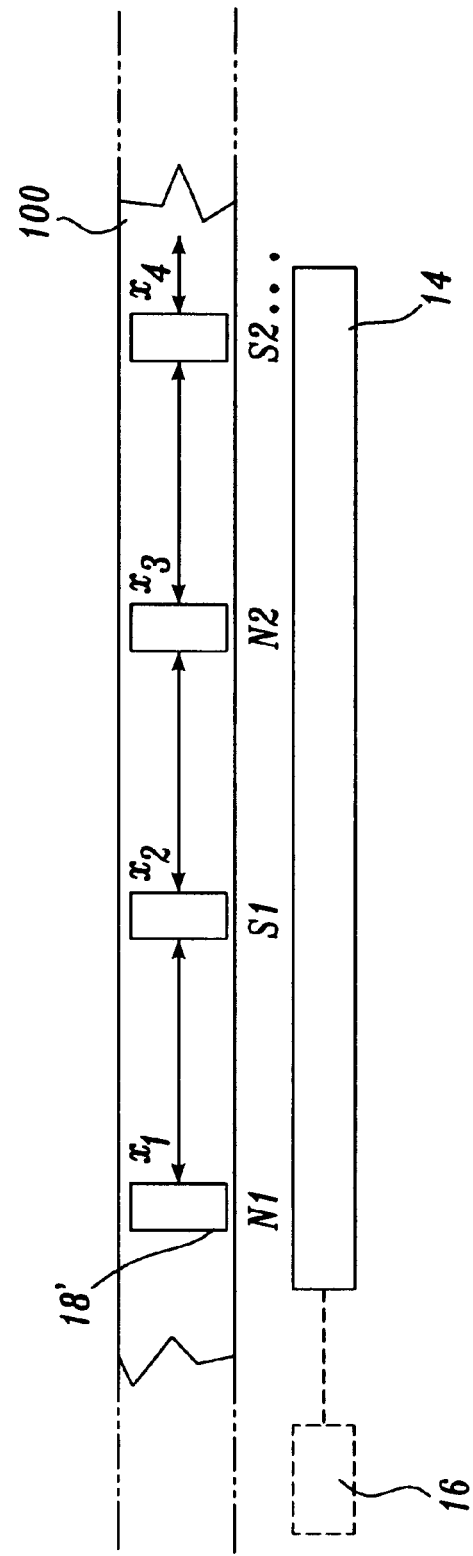
FIG. 16 is an enlarged diagrammatic side elevation thereof.

The present invention also can be used to accurately detect location of some target devices over a distance that greatly exceeds the length of the sensor array. This implies that the stroke to sensor length is greater than one. Such an application is illustrated diagramatically in FIGS. 15 and 16. As seen in FIG. 15, the target device 100 is several times longer than the sensing device 14. Sensing device 14 can be of the type previously described with reference to FIGS. 6 and 7. The sensing device provides the output for the processing device 16. In some applications the processing device can be incorporated in the same board as the sensing device 14, or it can be remotely located.

The target device 100 has incorporated in it a plurality of magnets or magnet arrays 18' of uneven spacing lengthwise of the target device, i.e., in the sensing or X direction. In the embodiment illustrated in FIG. 15, the target device travels linearly over the sensing device. The magnets 18' can be oriented alternately (south, north, south, and so on) and spaced unevenly so that for any given pair of magnets, the change in orientation (north to south, south to north, north to north, south to south) in combination with the distance between the magnets will be unique. The magnets 18' are spaced so that there will always be at least three magnets, which provide two distances, along the effective sensing area of the sensing device 14. In addition, it is desirable that the magnets not be located so close together that their magnetic fields interfere with each other to the extent that the preselected number of sensors are substantially affected by magnetic fields of adjacent magnets. More magnets along the sensor length provides for more codes.

In a representative embodiment, the overall length of the sensing device 14 can be about 9 inches with a usable scan length of 8 inches. A minimum spacing of 1.5 inches is effective to avoid interference between magnetic fields of adjacent magnets, and a maximum spacing of 3.5 inches assures that there always will be at least three magnets along the usable scan length of the sensing device. Thus, with reference to FIG. 16, the distances between adjacent magnets (such distances being represented as xl, x2, x3, x4 . . . ) can be selected to provide the desired coding. The first north to south transition (xl) can be 3.5 inches, for example, as can the first south to north transition (x2). Each succeeding transition can be 0.1 inch less than the last, i.e., the second north to south transition (x3) can be 3.4 inches and the second south to north transition (x4) can also be 3.4 inches. Codes would be selected to minimize error for any particular design, thus in actual application, adjacent codes would have maximum discrimination.

The processing device is programmed so that it will recognize a north to south transition of 3.5 inches as being within the corresponding segment of the target device 100. Thus, a very long stroke length for the target device can be accommodated by a relatively short sensing device. The processing device determines first the segment of the target device positioned over the sensing device and, next, the exact position of that segment relative to the sensing device. The change in orientation from one magnet to the next simply increases the allowable code set. In some applications, it may even be possible to use differing magnet strengths as another coding parameter.

The coding method to recognize the physical position of a long target over a short sensor can also be extended to the Y dimension. For example, a long magnet could extend directly in the Y direction. A second long magnet set could be going off at a slight angle to the first such that the distance between the first and second magnet sets increases in the Y direction. The first magnet set would detect the X distance, and the distance between the first and second set, would provide the Y distance. Additional distance coding could be obtained by alternating magnet directions and variance in magnet strength of sets.

Since Hall devices normally provide a signal proportional to field strength, the position sensing can be extended to X and Z, or X, Y, and Z.

Figure 17:
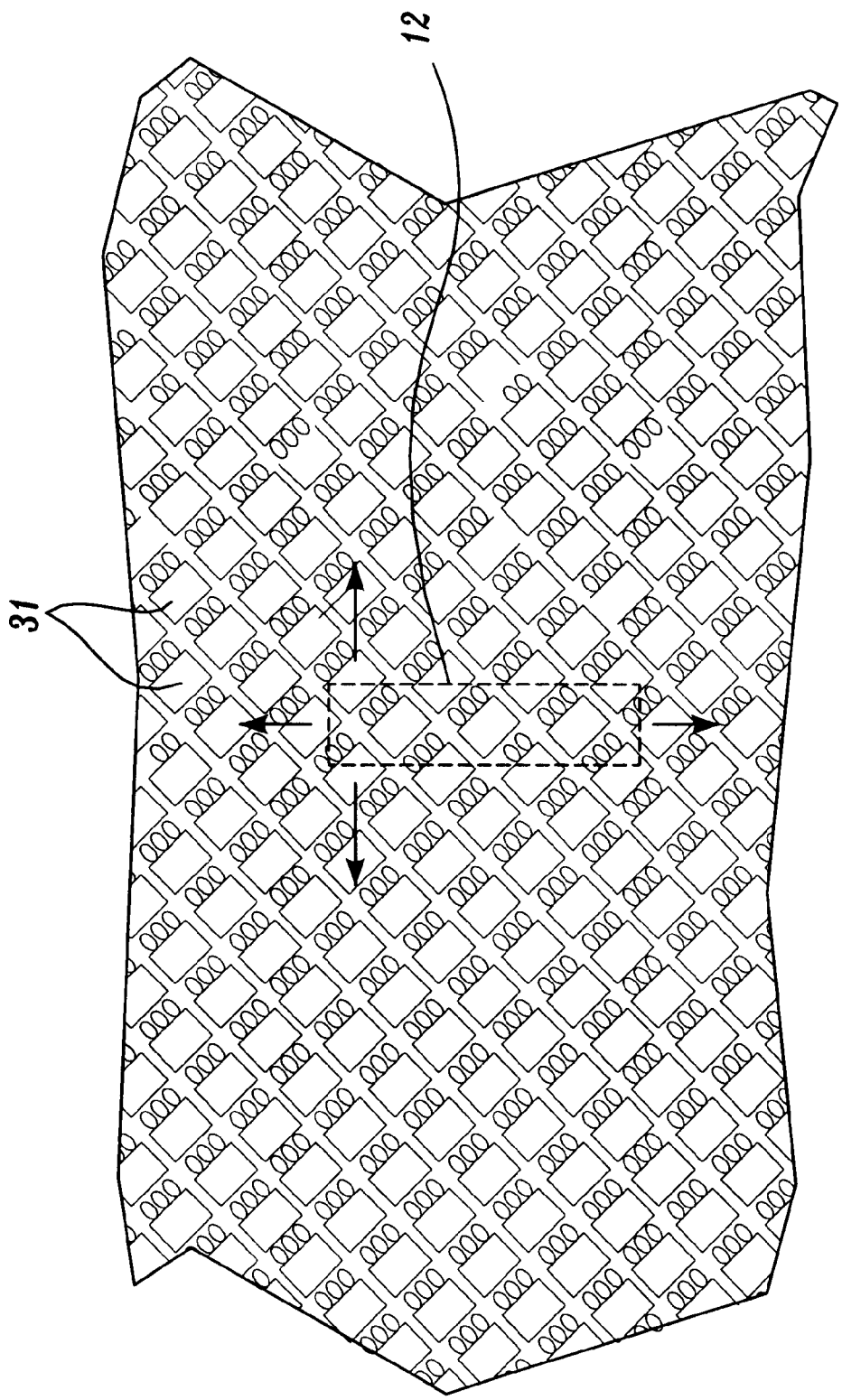
FIG. 17 is a fragmentary top plan of another embodiment of a sensing system in accordance with the present invention.

The linear array of Hall sensors of FIG. 6 can be extended in the Y direction to produce a two dimensional array of Hall sensors, as shown in FIG. 17. In so doing, it becomes an easy extension to determine not just the X position, but also the Y position of a simple target 12. For reference, the X direction can be considered horizontal in FIG. 17 and the Y direction vertical. The individual sensors 31 are arranged in rows and columns with their outputs multiplexed and provided to a processing devices. One method for determining the location of the target device relative to the two-dimensional array is to identify the target device having the highest output, and computing the X coordinate by evaluating the sensors of a preselected number at each side in the X direction, i.e., the appropriate "row" of sensors, using one of the methods described above. Similarly, the Y coordinate can be determined by using a predetermined number of sensors at each side in the Y direction, i.e., the appropriate "column" of sensors. Additionally, the Z dimension can be determined by the overall strength of the magnetic field which varies as the target device is moved perpendicular to the sensing device. Thus, the present invention can be used for determining location in one dimension (linear device), or in two dimensions or three dimensions. To further reduce X and Y location error, sensors arranged in one or more diagonal lines could be used for an independent location determination, and the mean of the separately calculated locations could be used as the final calculated location. Another possibility is to perform independent calculations for one or more adjacent rows and/or one or more adjacent columns. Another way the present invention can be used for detecting location in two or three dimensions is by providing simpler sensing arrays, of the type shown in FIGS. 6 and 7, for example, or even a linear row of side-by-side Hall effect sensors, and larger, more complicated target devices having magnets of different orientations and/or spaced apart in a unique pattern, similar to the spacing for the long stroke device illustrated in FIGS. 15 and 16, except that the arrays can be provided in two dimensions. For example, magnets of alternating polarities can be provided in rows and columns so that, for a given sensing array, two dimensional location can be determined based on the known orientation and spacing for the rows and columns as the two parts are moved relative to each other. Similar to the system shown in FIG. 17, the third dimension (Z coordinate) can be calculated based on change in magnetic field strength. It is likely that the magnet or magnets used in the target will have temperature coefficients, and thus the calculated Z location would change with temperature. Ways to correct this calculation include measuring temperature and correcting the calculation accordingly.

In some applications, the two parts whose respective locations it is desired to measure will not travel linearly relative to each other. For example, if the path of one part is arcuate relative to the other, the arcuately traveling part can have an array of Hall effect sensors along the same arc that passes adjacent to the other part, or one or more magnets can be arranged in an arc adjacent to the sensor array. Further, the present invention can be used to detect the rotative position of a rotary member, and, by calculation based on a series of readings, the speed of rotation and acceleration or deceleration.

Figure 18:
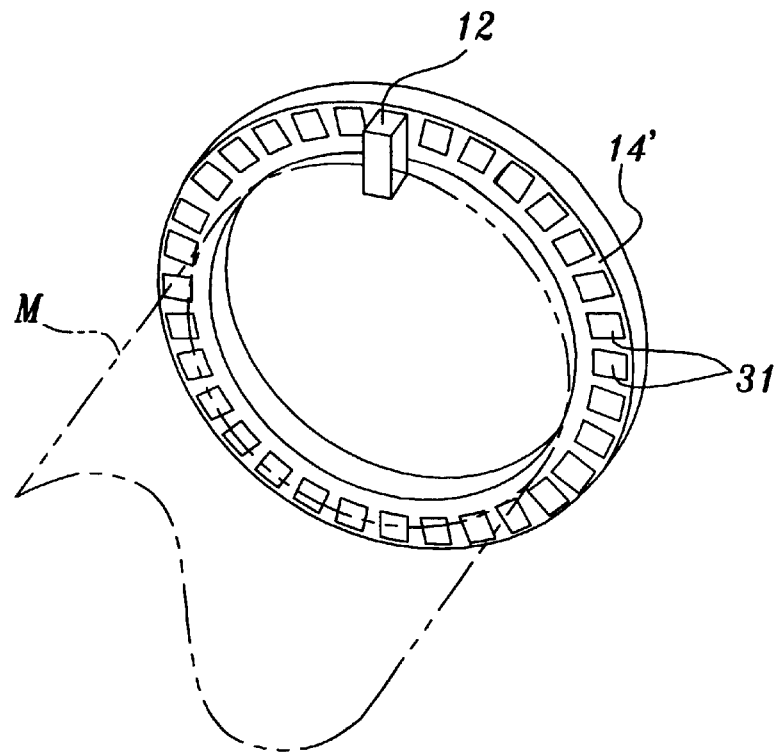
FIG. 18 is a diagrammatic top perspective of another embodiment of noncontacting position indicating components in accordance with the present invention, in which one component rotates relative to the other.

For example, with reference to FIG. 18, a circular sensing array 14' can be provided to detect the position of a magnetic target 12 mounted on a rotatable member represented by broken line M. Conventional microprocessors are able to update the location information quickly. Typical update times are 1000 times per second, and update times of 10,000 to 100,000 times per second (or even quicker) are achievable with Digital Signal Processors (DSP). Thus, at any instant the system of FIG. 18 can indicate the angular position of the rotary member, and can compare consecutive or a series of positions to calculate the speed of rotation or acceleration.

One application of such a device would be to improve upon the wheel speed sensing element of an aircraft antiskid system, wherein this invention can provide a more accurate, faster responding, lighter weight, less expensive method that those in use currently.

The higher position computation speed alone is a significant attribute of this invention. For control systems, such as are used in high performance aircraft, high-speed position information reduces time latency and improves stabilization and maneuvering abilities of the aircraft. High-speed position information is also beneficial in industry, where motor controls, high-speed manufacturing, and the like can be aided.

Figure 19:
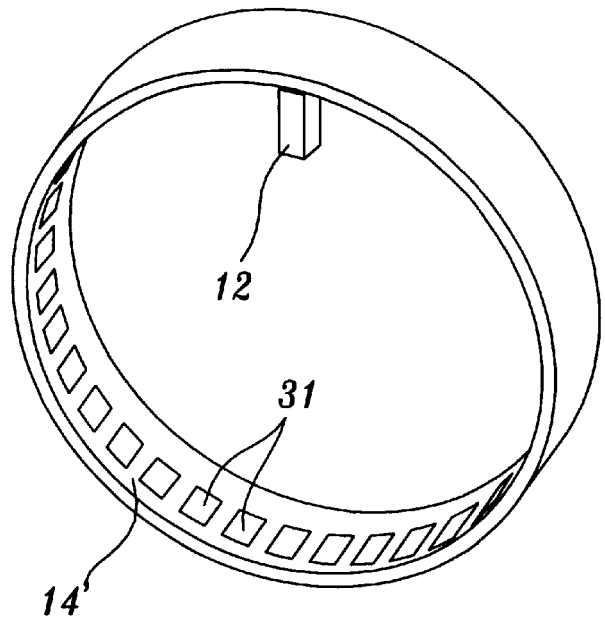
FIG. 19 is a top perspective of another embodiment of noncontacting position indicating components in accordance with the present invention, where one component rotates relative to another.
Figure 20:
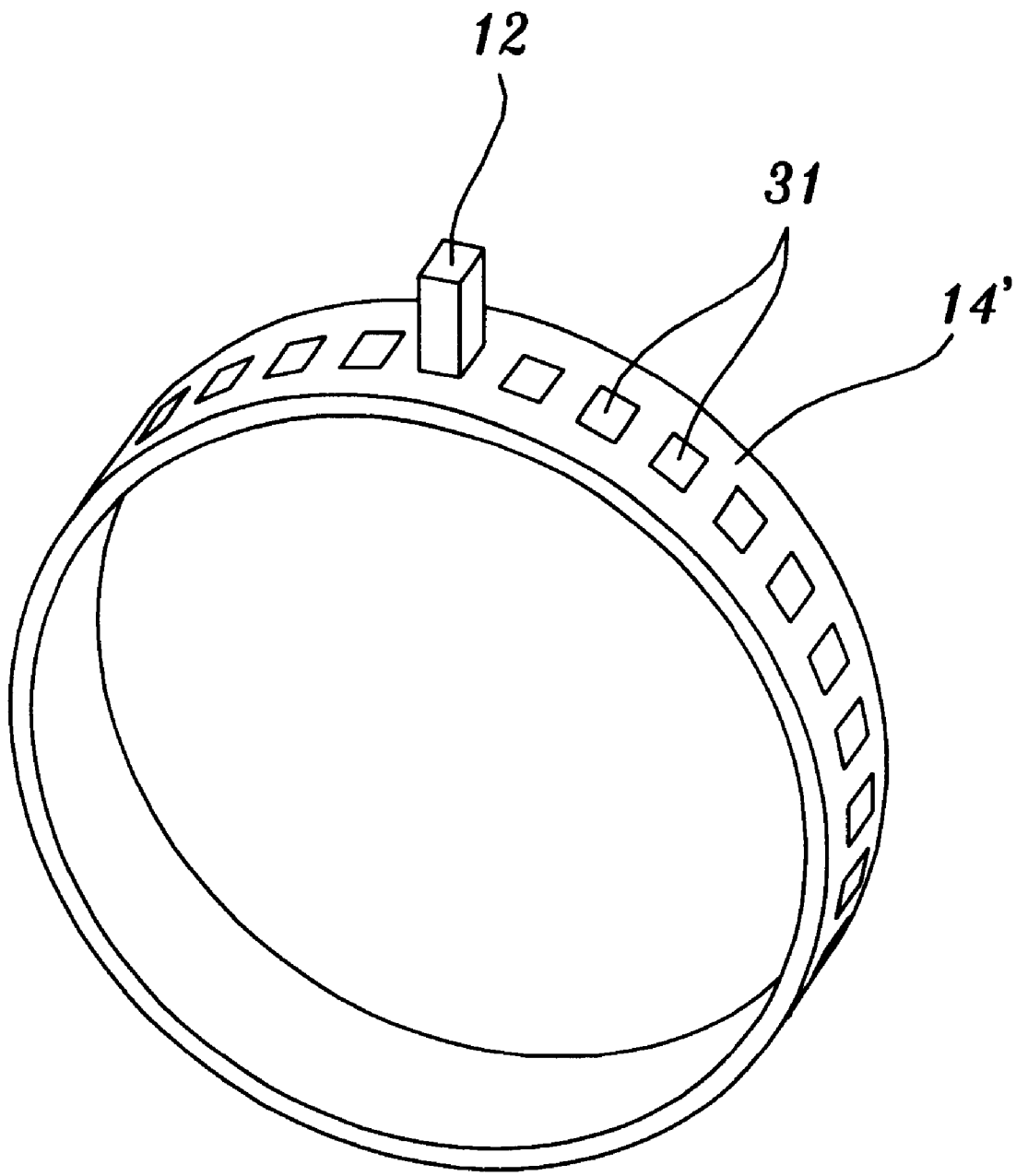
FIG. 20 is a top perspective of yet another embodiment of noncontacting position indicating components in accordance with the present invention, where one component rotates relative to another.

For rotary devices, other relative positions of the target device and sensing device can be used. For example, FIG. 19 illustrates a target device 12 positioned inside a cylindrical sensor array 14' of a sensing device, whereas FIG. 20 illustrates a target device 12 positioned outside a cylindrical sensing device 14' having a circumferential array of individual Hall effect sensors. Either of such devices can be carried by the rotating member of a mechanical system, although it generally will be preferable for the target device to be carried by the rotary member to simplify coupling of the outputs of the Hall effect sensors to a processing device.

In a rotating system, greater accuracy can be obtained and/or a greater distance between individual sensors can be used by positioning more than one target device along the circular path of relative movement. North-south coding can also be used. For example, a "primary" target device can be provided of one orientation, such as to produce a north pole magnetic field directed toward the sensing device, with a "secondary" target device of the opposite orientation positioned 180° from the primary target device and two additional secondary target devices of such opposite orientation at 90° to each side. The processing device then can distinguish the primary target device from the secondary devices and still have increased accuracy provided by four different calculations of the relative location and/or for independent calculations of the speed of rotation or acceleration.

Figure 21:
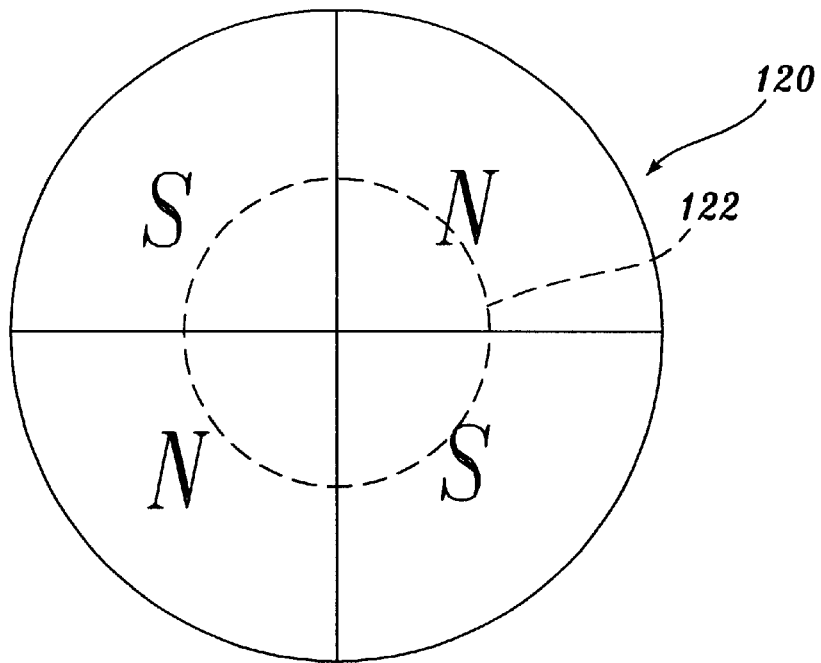
FIG. 21 is a diagrammatic top plan of an alternative magnet array for a target device usable in the present invention.
Figure 22:
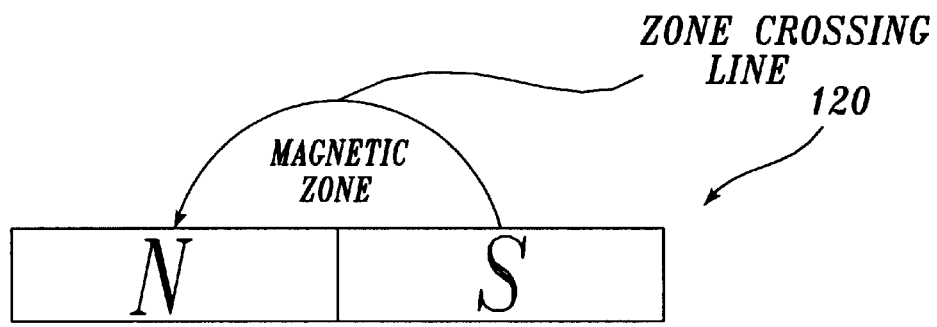
FIG. 22 is a side elevation thereof.

FIGS. 21 and 22 show the use of large magnet target array which might be used to detect zero crossing in a rotary system while providing a greater Z range allowed variance. In this target, the number of sections can be 2, 4, 6, 8 for example, again providing multiple locations for position detection. Further, in this method, all the Halls can be used in making the position computation leading to significantly higher position accuracy. For example, the sensors can be arranged in a circle 122 and a four section solid target would produce a signal appearing as a two cycle sine or square wave, depending on the Z distance. The position of these signals would be minimized against the Hall device readings, and the resulting answer would indicate position moved. This method can only indicate true angular position if there are only two magnet sections, however for many applications, it is only velocity that is important and more magnet sections can be used to improve the velocity accuracy.

Figure 23:
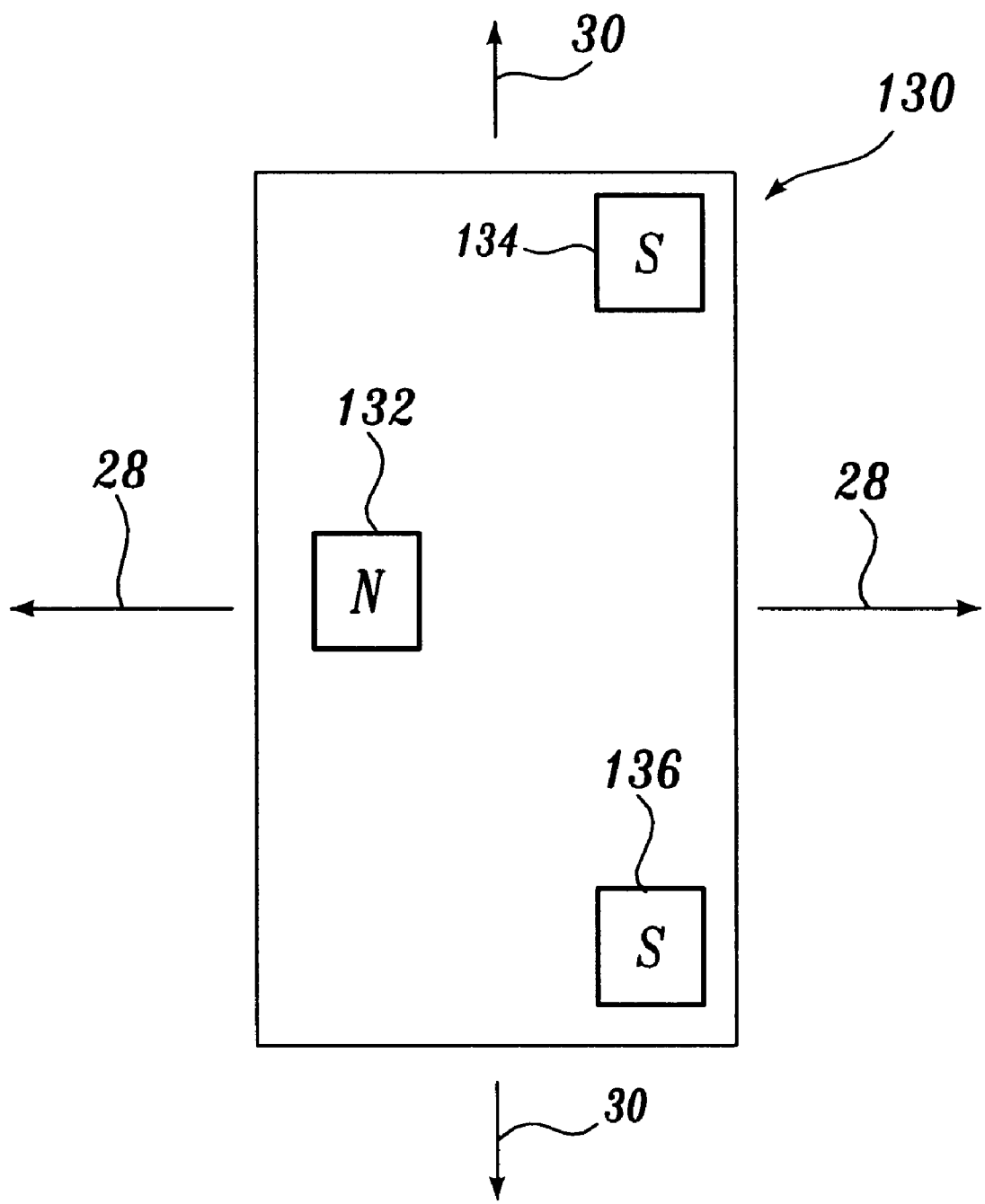
FIG. 23 is a diagrammatic top plan of another embodiment of a target device that can be used in the present invention.

Another application for the present invention is to determine relative attitude of two parts instead of or in addition to relative location. One way that this can be done is by use of a target having three or more magnet sources arranged nonlinearly over a sensor array so that independent, three-dimensional locations can be computed for the three sources. For example, FIG. 23 illustrates a target 130 having magnets 132, 134 and 136 in a generally triangular configuration. For purposes of illustration, arrows 28 represent an X sensing direction and arrows 30 represent a Y sensing direction. Target 130 can be mounted on a part situated adjacent to a two-dimensional sensing array of the general type shown in FIG. 17, for example. Location in terms of X, Y and Z coordinates can be computed for each of the target magnets 132, 134 and 136 using one or more of the methods described above. From these coordinates, the attitude of the target 130, can be computed. In addition, preferably one of the target magnets, such as magnet 132, has a different polarity so that the attitude information is nonambiguous and the actual orientation of the target 130 relative to the sensing array is known.

More specifically, FIG. 23 indicates a "neutral" attitude of target 130 over a sensing array with yaw, pitch and roll angles all equal to zero. In this case, Z coordinates for all three target magnets will be the same, and Y coordinates for magnets 134 and 136 will be the same. X coordinates will differ by the known spacing between the respective magnets. If the only change to the attitude of the target 130 is rotation about an axis perpendicular to the sensing array, corresponding to a change in yaw angle, the Z coordinates for the three magnets will remain the same and the degree of rotation is detectable by the change in relative X, Y coordinate values for any two magnets. If the only change from the position of FIG. 23 is a change in pitch, Z coordinates for magnets 134 and 136 would remain the same, but the Z coordinate for magnet 132 would be different. The pitch angle can be calculated based on this change. A roll movement would result in magnets 134 and 136 having Z coordinates at opposite sides of the Z coordinate for magnet 132. Since three points always define a plane, the attitude of the target 130 can be computed by evaluating the location information for the individual target magnets.

For a specific application, it may be possible to obtain a desired attitude measurement without performing independent location calculations for a multiplicity of target magnets. For example, a magnet elongated in the Y direction, such as that shown in FIG. 1, will produce a characteristic curve in the direction of its length. When placed over a two-dimensional array of the type shown in FIG. 17, a change in yaw position can be detected by evaluating outputs of a group of sensors around the sensor detecting the greatest magnetic field. The characteristic curve of the target magnet array will lie other than directly along a linear column in the Y direction if the yaw angle is changed. This variation can be detected and calculated based on the outputs of the sensors. For example, one way this can be done is to calculate the X position along more than one row and/or the Y position along more than one column and use the results to determine the yaw angle.

In the case of pitch or roll, a target oriented in the Y direction, for example, but angled along its length or to one side or the other would exhibit a characteristic change in the shape of the magnetic field as detected by the array of sensors. Evaluating the outputs of a plurality of rows and/or columns, or evaluation of the outputs of a cluster of sensors beneath the target will reveal the degree of pitch or roll. This shape will be dependent on the target used, such as the number and location(s) of the target magnet(s) and the dimensions of the magnetic field producing portion of the target as compared to the sensor array.

While the preferred embodiment of the invention has been illustrated and described, it will be appreciated that various changes can be made therein without departing from the spirit and scope of the invention. For example, in this disclosure, emphasis has been placed on the use of linear Hall Effect devices. Other methods of magnet field detection exist, but not all provide the advantages that Hall devices provide. Earlier attempts were made at using GMR (Giant Magneto Resistive) components, but it was determined at the time that the Hall devices were superior for this application. If in the future, the GMR parts are improved, or other linear magnet components show favor, they would be considered as part of this application. Also, the use of separate components for multiplexing, computation, etc. could be included into one component.

The embodiments of the invention in which an exclusive property or privilege is claimed are defined as follows:

1. A position indicating system comprising:
a first part having a target device producing a magnetic field;
a second part having a sensing device including an elongated array of sensors producing respective outputs that vary as a function of magnetic field strength, the first part being movable lengthwise relative to the elongated array of sensors of the second part with the target device adjacent to the sensing device; and
a processing device receiving the outputs of the sensors for calculating the relative positions of the first and second parts based on the outputs of several of the sensors, the processing device including a processor programmed to scan the outputs of the sensors, determine the sensor having the output indicating the greatest magnetic field strength, and determining the relative positions of the first and second parts based on the outputs of a predetermined number of sensors at each side of the sensor having the output indicating the greatest magnetic field strength.

2. The system defined in claim 1, in which the first and second parts are movable linearly relative to each other, the direction of relative movement of the first and second parts defining a sensing direction, and the array of sensors of the sensing device being elongated in the sensing direction.

3. The system defined in claim 2, in which the sensors of the array are spaced known distances from each other in the sensing direction.

4. The system defined in claim 2, in which the sensors of the array are spaced uniformly in the sensing direction.

5. The system defined in claim 3, in which the sensors are arranged in a plurality of rows extending lengthwise of the sensing direction.

6. The system defined in claim 4, in which the sensors of each row are spaced uniformly, and the sensors of adjacent rows are staggered relative to each other.

7. The system defined in claim 1, including an enclosure enclosing the first part, the sensing device being mounted outside of the enclosure.

8. The system defined in claim 1, in which the first part is elongated and has a plurality of target devices spaced lengthwise thereof.

9. The system defined in claim 8, in which the target devices of the first part are spaced apart a distance less than the length of the elongated array of sensors of the sensing device.

10. The system defined in claim 9, in which the target devices of the first part are spaced irregularly along the length of the first part, and the target devices having north-south orientations such that the distance and orientation difference between any two adjacent target devices is unique along the length of the first part.

11. The system defined in claim 1, in which the first part and the second part are movable nonlinearly relative to each other.

12. The system defined in claim 11, in which the first and second parts are rotatable relative to each other, the sensors of the sensing device being arranged in a circular array.

13. The system defined in claim 11, in which the target device includes a plurality of magnets having different respective north-south orientations.

14. The system defined in claim 1, in which the sensors of the sensing device are arranged in a two-dimensional array.

15. The system defined in claim 1, in which the processing device receives the outputs of the sensors and calculates the location of the first part relative to the second part in one dimension.

16. The system defined in claim 1, in which the processing device receives the outputs of the sensors and calculates the location of the first part relative to the second part in two dimensions.

17. The system defined in claim 1, in which the processing device receives the outputs of the sensors and calculates the location of the first part relative to the second part in three dimensions.

18. The system defined in claim 1, in which the processing device receives the outputs of the sensors and calculates relative attitude of the first part and the second part in at least one of pitch, yaw and roll.

19. The system defined in claim 1, in which the processing device receives the outputs of the sensors and calculates the location of the first part relative to the second part in at least one dimension and also relative attitude in at least one of pitch, yaw and roll.

20. A method for determining the position of a first part relative to a second part which comprises:

provﾠiding the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including determining which of the sensors has the output indicating the greatest magnetic field strength, and limiting the processing to such sensor and a predetermined number of sensors adjacent to such sensor.

21. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, in which the sensors provide outputs proportional to magnetic field strength, and including processing the outputs of several of the sensors by calculating the mean output for selected sensors.

22. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including measuring the offset for all sensors, storing the offset values and using the offset values when processing the outputs to determine the relative positions of the first and second parts.

23. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including adjusting the outputs of selected sensors based on stored gain values.

24. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including processing the outputs of the sensors by determining a nonlinear function fit for the outputs of selected sensors.

25. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including performing a calibration sequence and error correction analysis for use in the processing of the outputs of the several sensors to determine relative positions of the first and second parts.

26. A method for determining the position of a first part relative to a second part which comprises:

providing the first part with a target device producing a magnetic field;

providing the second part with a sensing device including an array of sensors producing respective outputs that vary as a function of magnetic field strength, the first part being movable relative to the second part with the target device adjacent to the sensing device; and processing the outputs of the sensors to calculate relative positions of the first and second parts based on the outputs of several of the sensors, including processing the outputs of the sensors at different times and calculating change in relative positions of the first and second parts to determine at least one of speed and acceleration of movement of one of the parts relative to the other part.

27. The method defined in claim 24, including processing the outputs of the sensors by calculating a Gaussian function fit for the outputs of several of the sensors.

28. A position indicating system comprising:

a first elongated part having a plurality of target devices producing magnetic fields and spaced lengthwise thereof;

a second part having a sensing device including an elongated array of sensors producing respective outputs that vary as a function of magnetic field strength, the first part being movable relative to the second part with the target devices adjacent to the sensing device, the target devices of the first part being spaced apart a distance less than the length of the elongated array of sensors of the sensing device; and a processing device receiving the outputs of the sensors for calculating the relative positions of the first and second parts based on the outputs of several of the sensors.

29. The system defined in claim 28, in which the target devices of the first part are spaced irregularly along the length of the first part, and the target devices having north-south orientations such that the distance and orientation difference between any two adjacent target devices is unique along the length of the first part.

* * * * *